United States Patent [19]

Rothstein

[11] Patent Number: 5,448,898
[45] Date of Patent: Sep. 12, 1995

[54] AIR TREATMENT PLANT FOR FOODSTUFF COMPRISING A TROUGH WITH AN ADJUSTABLE WIDTH

[75] Inventor: Sven-Olle Rothstein, Angelholm, Sweden

[73] Assignee: Frigoscandia Equipment Aktiebolag, Helsingborg, Sweden

[21] Appl. No.: 211,399

[22] PCT Filed: Oct. 2, 1992

[86] PCT No.: PCT/SE92/00690
§ 371 Date: Apr. 1, 1994
§ 102(e) Date: Apr. 1, 1994

[87] PCT Pub. No.: WO93/07429
PCT Pub. Date: Apr. 15, 1993

[30] Foreign Application Priority Data
Oct. 3, 1991 [SE] Sweden .................... 9102862

[51] Int. Cl.6 .............................................. F25D 25/04
[52] U.S. Cl. ................................... 62/380; 62/57; 62/63
[58] Field of Search ............... 62/374, 380, 63, 57; 165/104.16; 34/359, 576

[56] References Cited

U.S. PATENT DOCUMENTS

| 3,115,756 | 12/1963 | Overbye | 62/57 |
| 3,393,532 | 7/1968 | Khoylan . | |
| 3,691,644 | 9/1972 | Schnitzer | 62/57 |
| 4,164,129 | 8/1979 | Stuber . | |
| 4,283,923 | 8/1981 | Gruda et al. | 62/57 |
| 4,301,659 | 11/1981 | Martin et al. | 62/57 |

FOREIGN PATENT DOCUMENTS 2063184  7/1971  Germany .
442672  1/1986  Sweden .

Primary Examiner—Ronald C. Capossela
Attorney, Agent, or Firm—Browdy and Neimark

[57] ABSTRACT

A foodstuff air treatment device includes a housing (1) with an elongated trough (11) for receiving the foodstuffs to be treated. The trough extends through the housing and includes a foraminated bottom (15), a first side wall (17), and a second side wall (16). A heat exchanger (12) is disposed in the housing, and a fan assembly (13) is also disposed within the housing for producing an air flow that circulates through the heat exchanger, up through the trough, and back to the heat exchanger. One side wall (17) of the trough is adjustable, laterally to the length of the trough, for changing the width of the trough.

18 Claims, 3 Drawing Sheets

AIR TREATMENT PLANT FOR FOODSTUFF COMPRISING A TROUGH WITH AN ADJUSTABLE WIDTH

The present invention generally relates to an air treatment plant for foodstuffs, comprising a housing, an elongate trough provided therein for receiving the foodstuff to be treated, a heat exchanger and a fan assembly for producing an air flow circulating through the heat exchanger, up through the trough and back to the heat exchanger.

The invention relates especially to a freezing plant, but is also applicable to other air treatment plants, e.g. for cooling, drying and heating. In the freezing plant, the heat exchanger is a cooling-coil battery.

Previously known freezing plants of this type use a trough with a foraminated bottom, and in some cases also a foraminated conveyor belt running over the foraminated bottom or, alternatively, replacing it. The perforations in the trough bottom may be so dimensioned that at least some foodstuffs are caused to fluidise in the trough, this increasing the freezing speed and preventing the individual food products, e.g. peas, from freezing on to each other. Alternatively, the perforations may be so dimensioned that no fluidisation is brought about, but instead an agitation, which may sometimes be sufficient for preventing the food products from freezing on to each other and which, for certain difficultly-fluidisable foodstuffs, is the only feasible option.

Thus, the known freezing plants often suffer from considerable limitations in respect of freezing mode, i.e. fluidising or non-fluidising, and also in respect of the types of foodstuffs that can be treated. Further, they are limited as to the amount of foodstuff treated per unit of time, and are unable to cope with large variations in foodstuff quantity. To meet the demands of food producers several freezing plants may thus be required which operate in different ways and which have different capacities, both in respect of the type of foodstuff to be treated and in respect of the treated amount per unit of time.

The above description of prior-art freezing plants generally applies to known air treatment plants of the type stated by way of introduction.

The object of the present invention therefore is to improve an air treatment plant of the type stated in the introduction to this specification, with a view to making it adaptable to different modes of operation, different foodstuffs and different capacity requirements.

According to the invention, this object is achieved in that one side wall of the trough is adjustable sideways to change the width of the trough.

In this manner, the volume of the trough can be easily changed, which allows adjusting the treated amount of foodstuff per unit of time to a desired amount without changing the mode of operation, i.e. fluidising or non-fluidising. For larger trough widths, a non-fluidising mode of operation, which normally requires a smaller depth of the bed of treated foodstuff present in the trough, can also be used without the total amount of foodstuff treated per unit of time becoming less than in a fluidising mode of operation, which requires a larger bed depth and usually a smaller trough width in view of the maximum capacity of the fan assembly.

By making the air flow capacity of the fan assembly adjustable, preferably depending on the width of the trough, the adaptability of the air treatment plant can of course be further improved.

Thus, with a single air treatment plant according to the invention it becomes possible to replace several air treatment plants of conventional type.

In a preferred embodiment of the air treatment plant according to the invention, the adjustable side wall connects upwards to a boundary wall in a duct for the air flow. The side wall may then be movable together with or relative to the boundary wall. In the latter case, the side wall may be movable in the transverse direction of the trough by being connected to the boundary wall through one or more intermediate walls. The relative mobility between the side wall and the boundary wall may be achieved in that the intermediate wall or walls are articulated and/or movably connected to each other and/or the side wall and the boundary wall, respectively.

In a particularly preferred embodiment, the side wall and the boundary wall and the intermediate wall or walls, respectively, are divided into several sections throughout the length of the trough. These sections may be individually movable, such that the trough width can be varied throughout the length of the trough.

By using a foraminated belt as the bottom of the trough, it is possible to imitate both the conventional trough having a fixed, foraminated bottom, i.e. in the case of a stationary belt, and the conventional trough having a fixed, foraminated bottom and a foraminated belt moving over it. Further, the foraminated belt according to the invention is advantageous when used as the sole bottom of the trough as compared with the perforated belts of the prior art, in which the air flow cannot be guided very accurately up through the trough and in which the pressure drop through the trough bottom cannot be adjusted very accurately either.

The invention, as especially applied to air treatment plants in the form of freezing plants, will be described in more detail hereinbelow with reference to the accompanying drawings.

Figure 1:
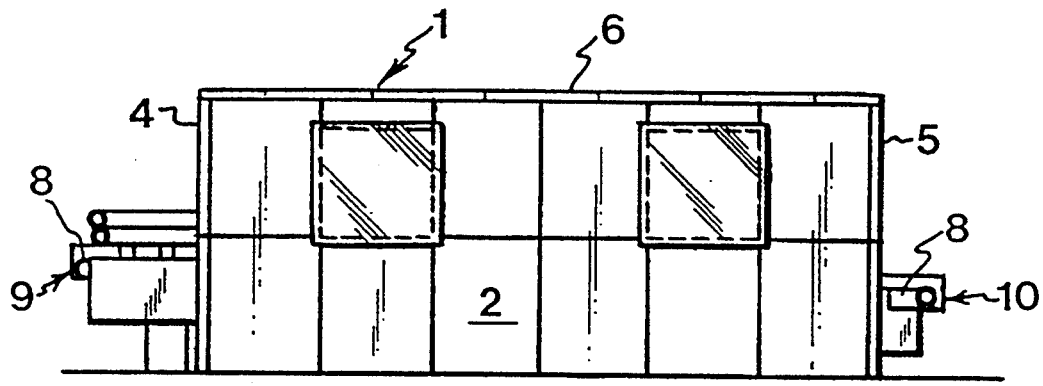
FIG. 1 is a schematic side view of a freezing plant according to the invention.
Figure 2:
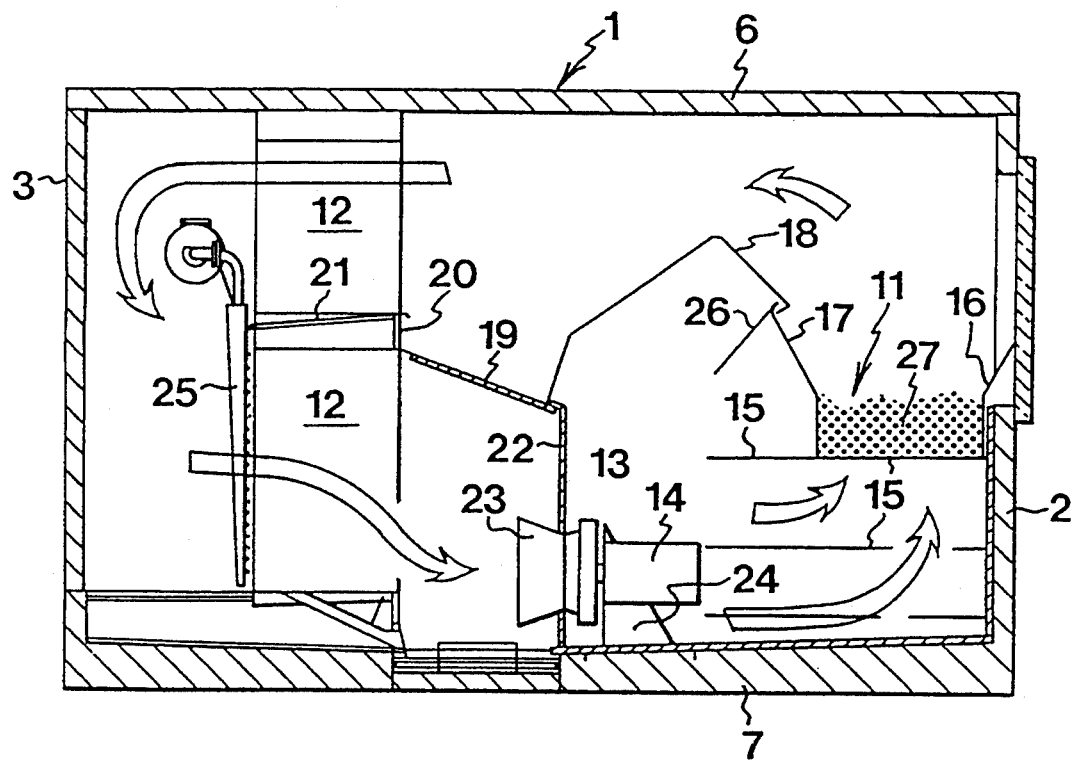
FIGS. 2 and 3 are cross-sectional views of the freezing plant in FIG. 1 and illustrate two different adjusting positions thereof.
Figure 3:
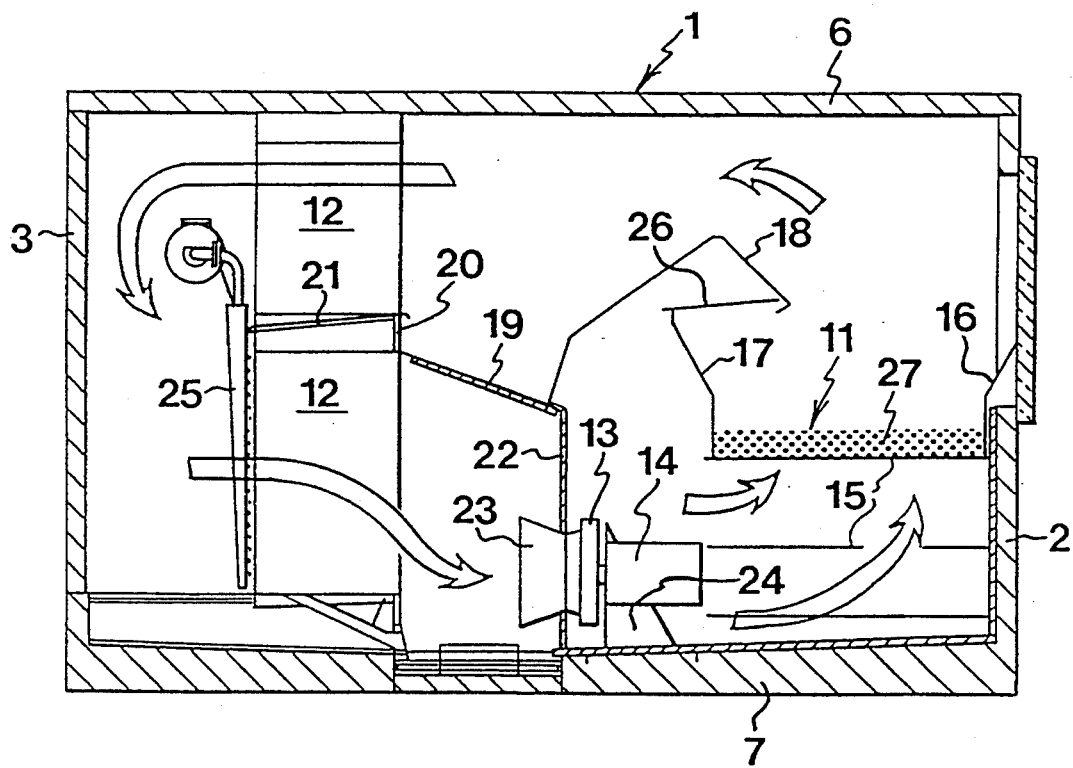

The embodiment of a freezing plant according to the invention as shown in FIGS. 1–3 has a housing 1 with side walls 2 and 3, end walls 4 and 5, a roof 6 and a bottom 7. The end walls 4 and 5 have openings for a belt conveyor 8 traversing the housing 1 and having an infeed station 9 and an outfeed station 10.

The housing 1 is divided into a number of substantially identical modules which extend transversely of the longitudinal direction of the belt conveyor 8, as disclosed in more detail in Swedish Patent Application No. 9102861-3.

As illustrated in FIGS. 2 and 3, the housing accommodates a trough 11, a cooling-coil battery unit 12 and a fan 13 with a fan motor 14. The bottom of the trough 11 is formed by the foraminated conveyor belt 15 of the belt conveyor 8. The outer side wall of the trough 11 is formed by the side wall 2 of the housing 1, this side wall having a lining 16 for providing a smooth surface. The inner side wall 17 of the trough 11 extends vertically upwards from the belt 15 through a distance which corresponds at least to the maximum bed depth in the trough 11, and is thereafter angled to form an air duct expanding over the bed. The air duct is defined between the inner side of the housing 1 and a boundary wall 18 connecting to the side wall 17, and additional boundary walls 19–22. The boundary wall 22 has an opening for a suction part 23 of the fan 13, which together with the motor 14 is mounted on the bottom 7 of the housing 1 by means of an angle attachment 24.

The fan assembly of the freezing plant consists of a number of fans 13 mounted throughout the length of the trough 11 and each having a motor 14. Similarly, the cooling-coil battery of the freezing plant consists of several cooling-coil battery units 12 disposed throughout the length of the trough 11. A defroster unit 25 may be arranged on the outside of the lower part of the cooling-coil unit 12, whose upper part can be excluded.

By the design described above, the fan assembly 13 produces an air flow according to the arrows in FIGS. 2 and 3, i.e. in a closed path through the cooling-coil battery unit 12, the fan assembly 13, up through the trough 11 and back to the cooling-coil battery unit 12. The side wall 17 is adjustable transversely of the longitudinal direction of the trough 11, between the end positions shown in FIGS. 2 and 3, whereby the width of the trough 11 can be continuously varied. To keep the air duct intact in all positions of the side wall 17, an intermediate wall 26 is provided between the side wall 17 and the boundary wall 18. The wall 26 is articulated to the boundary wall 18, more specifically at one of its longitudinal edges, and the upper longitudinal edge of the side wall 17 is movable in sliding contact with the underside of the intermediate wall 26. The connections between the side wall 17 and the intermediate wall 26 as well as between the wall 26 and the boundary wall 18 are arranged in a substantially air-tight manner so as to prevent short-circuiting of the air flow.

According to the invention, the capacity of the fan assembly 13 can also be changed for any adjusted width of the trough 11, whereby a number of different operational cases can be achieved. By way of example, the case shown in FIG. 2, in which the width of the trough 11 is the smallest width possible in this embodiment, relates to a fluidising mode of operation with a relatively large depth of the product bed 27 held in the trough 11. The operational case shown in FIG. 3, in which the width of the trough 11 is the largest width possible in this embodiment, relates to a non-fluidising mode of operation with a relatively small depth of the product bed 27.

It is understood that by varying the width of the trough 11 and the capacity of the fan assembly 13 it is possible to adapt the desired mode of operation, i.e. fluidising or non-fluidising, and the desired amount of foodstuff treated per unit of time to different types of foodstuffs. Another variable is the motion pattern of the belt 15. Thus, the belt 15 may either be held stationary, thus obtaining a trough 11 with a fixed bottom, or travel forwards.

Figure 5:
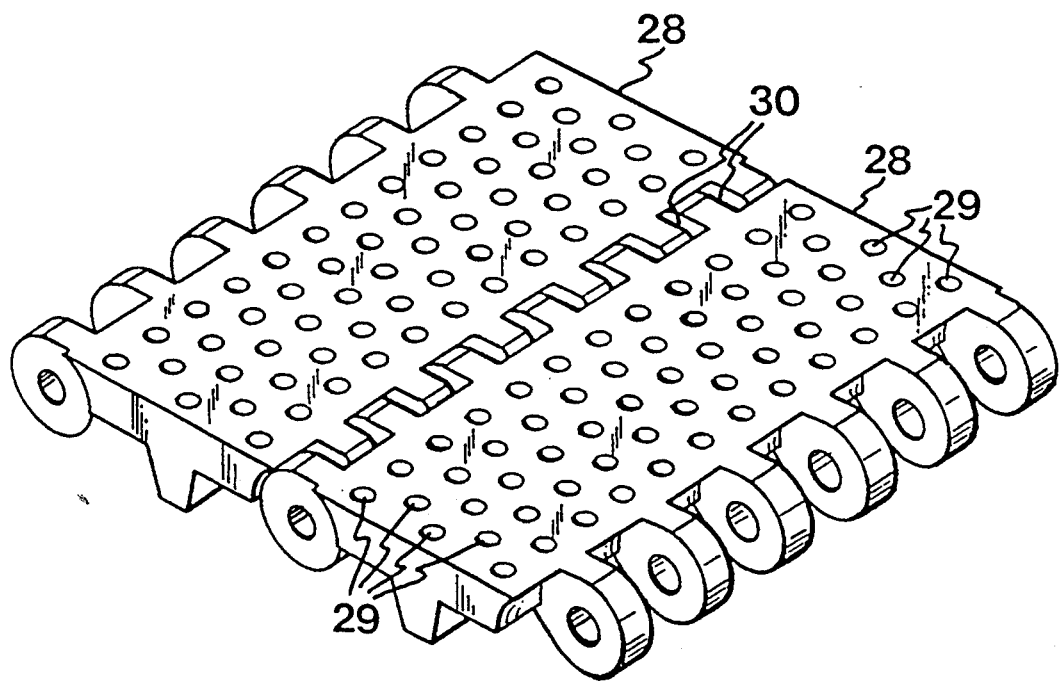
FIG. 5 shows parts of a foraminated conveyor belt which can be used in the freezing plant of the invention.

In the case of a fluidising mode of operation, the guiding of the air flow up through the bottom of the trough 11 is decisive of whether it is possible to transfer the bed 27 to and maintain it in a fluidising state or not. Prior-art freezing plants, using a perforated belt in the form of a wire net, provide inadequate guiding of the air flow to achieve a stable fluidised state. According to prior-art techniques, this requires a fixed bottom with specially dimensioned perforations. By using in the invention a foraminated belt of the type shown in FIG. 5, a stable fluidising state can be achieved with the foraminated belt alone. FIG. 5 shows more specifically two identical plates 28 which can be interconnected in an optional number, both longitudinally and transversely, to form a conveyor belt 15 of desired length and width. According to the invention, the plates 28 have perforations in the form of through holes 29 over their entire surface, as well as slots 30 along the articulated joint used for linking together the plates in the longitudinal direction of the belt 15. With a belt of the design as partially illustrated in FIG. 5, it is possible by the thickness of the plates 28 to obtain perforations which make it possible to accurately guide the air flow through the bottom, in the form of the belt 15, of the trough 11 and, hence, ensure a stable fluidising state.

The mobility of the side wall 17 in the transverse direction of the trough 11 can of course be achieved in ways other than that shown in FIGS. 2 and 3. Some variants for the displacement of the side wall 17 are illustrated in FIGS. 4A–F.

Figure 4A:
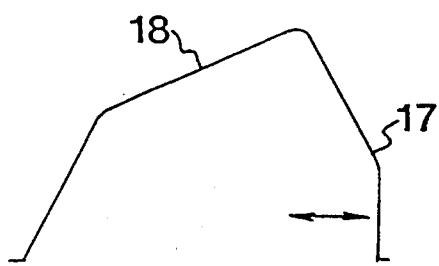
FIGS. 4A–4F illustrate different basic variants of displacement of a side wall in the freezing plant according to the invention.

As shown in FIG. 4A, the side wall 17 is fixedly connected to the boundary wall 18, which in this case is movable together with the side wall 17.

Figure 4B:
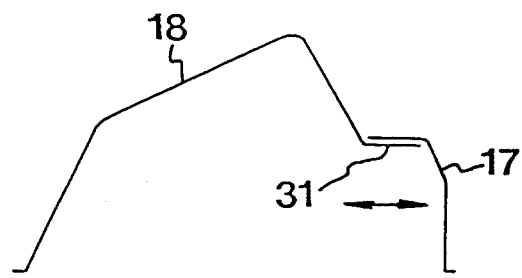
Figure 4C:
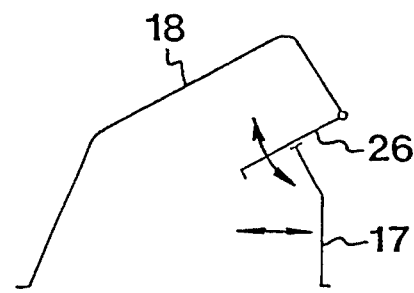
Figure 4D:
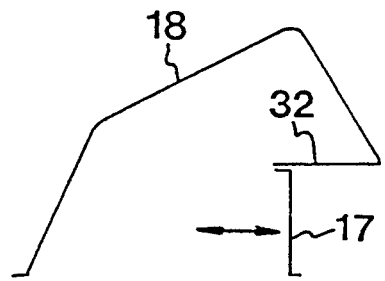

As shown in FIGS. 4B and 4D, the side wall 17 is displaceable in sliding contact, both with the bottom 15 of the trough 11 and with an extension 31 and 32, respectively, of the boundary wall 18, that is parallel to the bottom 15 of the trough 11.

FIG. 4C shows the same embodiment as in FIGS. 2 and 3.

Figure 4E:
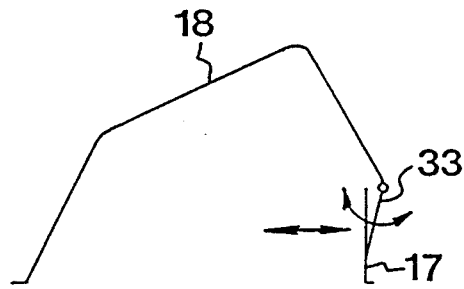

As shown in FIG. 4E, there is provided an intermediate wall 33 which is articulated to the boundary wall 18 and which is articulated and displaceably connected to the side wall 17.

Figure 4F:
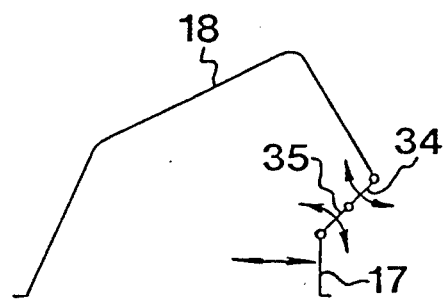

As shown in FIG. 4F, there are provided intermediate walls 34 and 35 which are articulated both to each other and to the side wall 17 and the boundary wall 18.

Just as the housing 1 is advantageously divided into modules, the side wall 17 and the walls connecting thereto may be divided into identical sections, each corresponding to a particular module, throughout the length of the trough 11. The different sections of the side wall 17, like the sections of the walls movable together with the side wall, may then be individually movable, such that the width of the trough 11 can vary throughout its length. A condition for this is, of course, that the different sections of the side wall 17, like the sections of the walls movable together with the side wall, have end wall portions so as to maintain the air flow duct intact.

When the freezing plant according to the invention is run by the fluidising mode of operation, some types of foodstuff require a given length-to-width ratio of the trough. A change of the trough width thus necessitates a change of the trough length, i.e. the length where fluidisation is to take place. Such a length adjustment can be achieved in the invention by means of some type of air barrier, e.g. a continuous plate, which is displaceable underneath the foraminated trough bottom, preferably formed by a conveyor belt. This length adjustment is suitably carried out at the outfeed end of the freezing plant, such that the air circulation through the trough is limited there throughout a portion of the trough length.

It is evident that the invention is not restricted to the particular embodiment of a freezing plant described above, but can also be used in freezing plants with another mutual location of the components included, as in troughs with a bottom of conventional design.

Finally, it should be pointed out that the invention is applicable to air treatment plants in general, and is not restricted to freezing plants.

I claim:

1. An air treatment plant for foodstuffs, comprising: a housing (1); an elongate trough (11) provided within said housing and extending along a length thereof for receiving the foodstuffs to be treated, said trough including a foraminated bottom (15), a first side wall (17), and a second side wall (16), the first side wall and the second side wall defining a width therebetween; a heat exchanger (12) disposed within said housing; and a fan assembly (13) disposed within said housing for producing an air flow circulating through the heat exchanger, upwardly through the trough and back to the heat exchanger; wherein the first side wall (17) of the trough (11) is adjustable laterally to the length for changing the width of the trough.

2. The air treatment plant as claimed in claim 1, wherein an air flow capacity of the fan assembly is adjustable, as a function of the width of the trough (11).

3. The air treatment plant as claimed in claim 2 wherein the first side wall (17) connects upwards to a boundary wall (18) in a duct for the air flow.

4. The air treatment plant as claimed in claim 3, wherein the first side wall (17), and the boundary wall (18) and the intermediate wall or walls (26, 31-35), respectively, are divided into several, optionally individually movable sections through the length of the trough (11).

5. The air treatment plant as claimed in claim 4, wherein the bottom of the trough (11) comprises a foraminated belt (15), and an air barrier device, to prevent air circulation through an adjustable part of the trough length.

6. The air treatment plant as claimed in claim 5, wherein the bottom of the trough (11) consists of a foraminated belt (15).

7. The air treatment plant as claimed in claim 2, wherein the first side wall (17), and the boundary wall (18) and the intermediate wall or walls (26, 31-35), respectively, are divided into several, optionally individually movable sections through the length of the trough (11).

8. The air treatment plant as claimed in claim 2, wherein the bottom of the trough (11) comprises a foraminated belt (15), and an air barrier device, to prevent air circulation through an adjustable part of the trough length.

9. The air treatment plant as claimed in claim 2, wherein the bottom of the trough (11) consists of a foraminated belt (15).

10. The air treatment plant as claimed in claim 1, wherein the first side wall (17) is connected to a boundary wall (18), the first side wall and the boundary wall together comprising a baffle to direct air flow.

11. The air treatment plant as claimed in claim 10, wherein the first side wall (17) and the boundary wall (18) are movable as a unit.

12. The air treatment plant as claimed in claim 10, wherein the first side wall (17) is movable relative to the boundary wall (18).

13. The air treatment plant as claimed in claim 12, wherein the first side wall is laterally displaceable within a space between the bottom (15) of the trough (11) and an extension (31, 32) of the boundary wall (18) parallel to the bottom.

14. The air treatment plant as claimed in claim 12, wherein the side wall (17) is connected to the boundary wall (18) by at least one intermediate wall (33-35) articulating with selectively the first side wall, the boundary wall, and another one of the intermediate wall.

15. The air treatment plant as claimed in claim 14, wherein the side wall (17), the boundary wall (18) and the intermediate wall are divided into individually movable sections along the length of the trough (11).

16. The air treatment plant as claimed in claim 1, wherein the bottom of the trough (11) comprises a foraminated belt, and an air barrier device, to prevent air circulation through an adjustable part of the trough length.

17. The air treatment plant as claimed in claim 1, wherein the bottom of the trough (11) consists of a foraminated belt (15).

18. The air treatment plant as claimed in claim 1, wherein the air treatment plant is a freezing plant.

* * * * *